United States Patent
Ogura (12)

(10) Patent No.: US 9,572,489 B2
(45) Date of Patent: Feb. 21, 2017

(54) OPHTHALMOLOGIC IMAGING APPARATUS, OPHTHALMOLOGIC IMAGING METHOD, AND PROGRAM

(71) Applicant: CANON KABUSHIKI KAISHA, Tokyo (JP)

(72) Inventor: Hiraku Ogura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 273 days.

(21) Appl. No.: 14/049,515

(22) Filed: Oct. 9, 2013

(65) Prior Publication Data

US 2014/0104570 A1    Apr. 17, 2014

(30) Foreign Application Priority Data

Oct. 17, 2012   (JP) .................................. 2012-229454

(51) Int. Cl.
| | | |
|---|---|---|
| *A61B 3/14* | (2006.01) | |
| *A61B 3/10* | (2006.01) | |
| *A61B 3/12* | (2006.01) | |

(52) U.S. Cl.
CPC .. *A61B 3/12* (2013.01); *A61B 3/14* (2013.01)

(58) Field of Classification Search
USPC .......... 351/200, 205, 206, 209–211, 221, 22, 351/225, 243–246
See application file for complete search history.

(56) References Cited

U.S. PATENT DOCUMENTS

| | | | |
|---|---|---|---|
| 6,564,014 B1 * | 5/2003 | Takeuchi ................. | G03B 7/16 396/157 |
| 8,496,330 B2 | 7/2013 | Kamada | |
| 8,854,487 B2 | 10/2014 | Ikeda | |
| 8,857,989 B2 | 10/2014 | Iwanaga | |

(Continued)

FOREIGN PATENT DOCUMENTS

| | | |
|---|---|---|
| CN | 102188232 A | 9/2011 |
| CN | 102265603 A | 11/2011 |

(Continued)

OTHER PUBLICATIONS

Feb. 28, 2015 Chinese Official Action in Chinese Patent Appln. No. 201310486563.1.

(Continued)

*Primary Examiner* — Joseph P Martinez
*Assistant Examiner* — Brandi Thomas
(74) *Attorney, Agent, or Firm* — Fitzpatrick, Cella, Harper & Scinto

(57) ABSTRACT

A fundus camera, which does not take time for adjustment of illumination light amount and focusing even if brightness of the fundus is different for each eye to be inspected, includes an illumination unit for illuminating the fundus of the eye to be inspected, a photometry unit for performing photometry of reflection light from the fundus illuminated by the illumination unit, an illumination light amount control unit for controlling a light amount of the illumination unit, a focus detection area determining unit for determining (Continued)

a focus detection area with respect to a fundus image taken by an image pickup unit, and a focus detection unit for detecting a focus position in the area determined by the focus detection area determining unit. The photometry unit calculates a photometry value of the focus detection area, and the illumination light amount is controlled based on the photometry value.

17 Claims, 4 Drawing Sheets

(56) References Cited

U.S. PATENT DOCUMENTS

| | | | |
|---|---|---|---|
| 2004/0190890 A1* | 9/2004 | Osawa | G03B 7/08 396/234 |
| 2011/0090457 A1* | 4/2011 | Shikaumi et al. | 351/206 |
| 2011/0228128 A1 | 9/2011 | Ikeda | |
| 2011/0228220 A1 | 9/2011 | Kamada | |
| 2011/0292337 A1 | 12/2011 | Iwanaga | |
| 2012/0050679 A1 | 3/2012 | Kishida | |
| 2012/0154748 A1* | 6/2012 | Inoue et al. | 351/206 |

FOREIGN PATENT DOCUMENTS

| | | |
|---|---|---|
| CN | 102481097 A | 5/2012 |
| JP | H04-150831 A | 5/1992 |
| JP | 08-265629 A | 10/1996 |
| JP | 2007-108455 A | 4/2007 |
| JP | 2011-050531 A | 3/2011 |
| JP | 2011-250961 A | 12/2011 |

OTHER PUBLICATIONS

Aug. 24, 2015 Chinese Official Action in Chinese Patent Appln. No. 201310486563.1.

* cited by examiner

OPHTHALMOLOGIC IMAGING APPARATUS, OPHTHALMOLOGIC IMAGING METHOD, AND PROGRAM

BACKGROUND OF THE INVENTION

Field of the Invention

The present invention relates to an ophthalmologic imaging apparatus such as a fundus camera and an ophthalmologic imaging method used for a physical examination in a group checkup or a general checkup, and to a program therefore.

Description of the Related Art

Conventionally, a fundus examination is performed in a group checkup such as a resident checkup or a company checkup. Usually in fundus imaging in the group checkup, non-mydriatic imaging is performed, which does not need mydriatics. In the non-mydriatic imaging, an examination room is darkened, or a simple darkroom is used so that the eye to be inspected is shielded from indoor light, and thus natural mydriasis of the eye to be inspected is urged for imaging.

An ophthalmologic imaging apparatus that performs non-mydriatic fundus imaging includes an observation light source in an infrared wavelength range that usually does not cause miosis, and a visible imaging light source. In the fundus imaging, the observation light source is used for illuminating the fundus to perform positioning and focusing of the imaging apparatus. After that, an image is taken of the fundus illuminated by the imaging light source.

As to focusing, there is known a fundus camera of Japanese Patent Application Laid-Open No. 2011-50531 in which automatic focusing is performed on a specific section of the fundus of the eye to be inspected. In the fundus camera described in Japanese Patent Application Laid-Open No. 2011-50531, a focus evaluation value is calculated based on a focus state detection unit that detects contrast of a specific section in the fundus of the eye to be inspected, and the automatic focusing is performed on a focus position that is a position at which the focus evaluation value becomes maximum. In addition, the fundus camera of Japanese Patent Application Laid-Open No. 2011-50531 includes an illumination light amount control unit that adjusts the illumination light amount of the light source for observation as a technique for realizing more accurate automatic focus. The illumination light amount control unit controls the illumination light amount based on an output of the focus state detection unit.

When detecting contrast of the fundus of the eye to be inspected, because brightness of the fundus is different for each eye to be inspected, and because the light source for observation also has an individual variation, brightness of the fundus in observation has a variation. This variation also affects detection of a contrast value, and hence stable focus detection cannot be performed. Therefore, in order to perform stable focus detection, it is necessary to detect brightness of the fundus in advance and to adjust the illumination light amount in accordance with the brightness. In order to adjust the illumination light amount, it is necessary to detect the illumination light amount.

The fundus camera disclosed in Japanese Patent Application Laid-Open No. 2011-50531 uses a focus state detection unit so as to output the focus evaluation value based on the contrast calculated from a luminance value of each pixel in the fundus image, and detects a local maximum value of the focus evaluation value so as to perform focus evaluation. In addition, because the focus evaluation value refers to the luminance value of the fundus image, it is possible to detect whether or not the luminance value is saturated at the same time as the focus evaluation. If the luminance value is saturated, the illumination light amount is adjusted.

However, after starting the focus evaluation, if the illumination light amount is adjusted so as to change the observation condition for the fundus, the contrast value of the fundus image also changes. Therefore, it is necessary to search for the local maximum value of the focus evaluation value again. In this case, it takes time to obtain an in-focus state, or extra amount of light illuminates the eye to be inspected, which increases a load on an examiner or a subject.

SUMMARY OF THE INVENTION

According to one embodiment of the present invention, there is provided an ophthalmologic imaging apparatus, including: an illumination unit for illuminating a fundus of an eye to be inspected for observation and imaging; an image pickup unit for imaging the fundus of the eye to be inspected, which is illuminated through a focus lens; an illumination light amount control unit for controlling a light amount of the illumination unit for illuminating the fundus; a focus detection unit for detecting a focus position of the focus lens; and a photometry unit for performing photometry of reflection light from the fundus illuminated by the illumination unit. The photometry unit calculates a photometry value of the reflection light from the fundus. The illumination light amount control unit controls an illumination light amount based on the photometry value. The focus detection unit performs focus evaluation after the illumination light amount is controlled by the illumination light amount control unit.

In the ophthalmologic imaging apparatus according to one embodiment of the present invention, it is possible to detect brightness of the image of the fundus of the eye to be inspected before obtaining a focus evaluation value. Thus, it is possible to start the focus evaluation after illuminating the fundus of the eye to be inspected with brightness suitable for calculating the focus evaluation value. Therefore, it is possible to prevent in advance a focus detection error due to saturation of the luminance value or the like, and hence more stable and accurate focus detection can be performed.

Further features of the present invention will become apparent from the following description of exemplary embodiments with reference to the attached drawings.

DESCRIPTION OF THE EMBODIMENTS

Now, an ophthalmologic imaging apparatus according to an embodiment of the present invention is described in detail with reference to the attached drawings.

First Embodiment

The present invention is described in detail based on an embodiment illustrated in FIG. 1 to FIG. 6.

Figure 1:
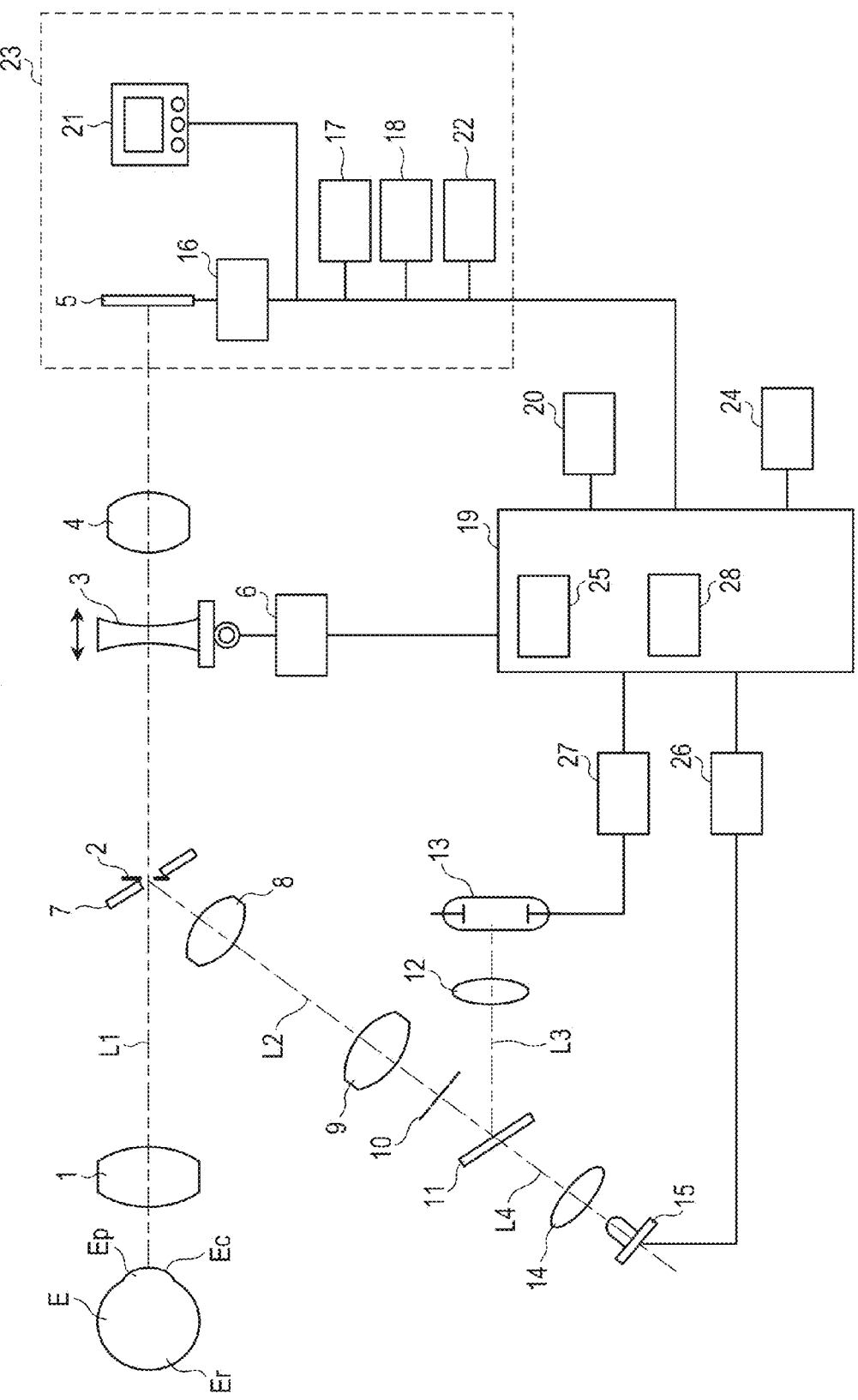
FIG. 1 is a structural diagram of an ophthalmologic imaging apparatus illustrating an embodiment of the present invention.

FIG. 1 is a structural diagram of a fundus camera as an ophthalmologic imaging apparatus according to the embodiment of the present invention. An objective lens 1 is disposed to be opposed to an eye to be inspected E. On an optical axis L1 of the objective lens 1, there are disposed an imaging stop 2, a focus lens 3, an imaging lens 4, and an image pickup element 5 having sensitivity to visible light and infrared light. The objective lens 1 to the imaging lens 4 constitute an observation/imaging optical system, which constitutes a fundus image observation image pickup unit together with the image pickup element 5. Reflection light containing visible light and infrared light from a fundus Er of the eye to be inspected E is guided to the image pickup element 5 through an optical path along the optical axis L1. Further, the focus lens 3 is connected to a focus lens moving portion 6 to move in the direction of the optical axis L1.

On the other hand, a perforated mirror 7 is disposed diagonally in a vicinity of the imaging stop 2. On an optical axis L2 in a reflection direction of the perforated mirror 7, there are disposed a lens 8 and a lens 9. In addition, on the optical axis L2, there are disposed a ring stop 10 that is disposed at a position substantially optically conjugate to a pupil Ep of the eye to be inspected E with respect to the lens 8 and the lens 9 and has a ring-like aperture with a light blocking portion in the optical axis center, and a dichroic mirror 11 having characteristics of transmitting infrared light and reflecting visible light. On an optical axis L3 of the dichroic mirror 11 in the reflection direction, there are disposed a condenser lens 12 and a stroboscopic light source 13 as an imaging light source that emits visible pulse light. On an optical axis 4 of the dichroic mirror in the transmission direction, there are disposed a condenser lens 14 and an infrared LED 15 (infrared light source) as an observation light source in which multiple infrared LEDs are disposed so as to emit infrared light as infrared stationary light. The objective lens 1 to the dichroic mirror 11, the condenser lens 12, and the condenser lens 14 constitute a fundus illumination optical system. This fundus illumination optical system, the stroboscopic light source 13 as the imaging light source, and the infrared LED 15 as the observation light source constitute a fundus illumination unit. In this embodiment, the stroboscopic light source 13 is a wide-band wavelength light source having a wavelength of 420 nm to 750 nm, and the infrared LED 15 is a single wavelength light source having a wavelength of 850 nm.

The fundus image observation image pickup unit and the fundus illumination unit described above are housed in one casing and constitute a fundus camera optical portion. Further, the fundus camera optical portion is placed on a sliding table (not shown) and is capable of being aligned with the eye to be inspected E.

In addition, an output of the image pickup element 5 is converted into a digital signal by an A/D converter element 16 to be stored in a memory 17 and output to a photometry value calculation unit 18, each of which is connected to a system control portion 19 such as a CPU for controlling the entire apparatus. The system control portion 19 is connected to an image memory 20, and a still image taken by the image pickup element 5 is stored as a digital image. The image pickup element 5, the A/D converter element 16, the memory 17, and the photometry value calculation unit 18 constitute an image pickup unit 23 together with a monitor 21 for displaying an infrared observation image and a visible image taken by the image pickup element 5, and an image pickup unit control portion 22. Further, this image pickup unit 23 is removably fixed to the casing of the fundus camera optical portion by a mount portion (not shown).

Further, the system control portion 19 is connected to the focus lens moving portion 6 and an operation input portion 24 so as to control the position of the focus lens 3 on the optical axis L1. Note that, this embodiment is described as an apparatus having an automatic focus function for automatically performing focus adjustment. In a manual focus mode, the focus lens moving portion 6 is controlled based on an operation input of the operation input portion 24. In addition, in an automatic focus mode, the focus lens moving portion 6 is controlled based on a result of the detection by a focus detection portion 25 in the system control portion 19.

On the other hand, the infrared LED 15 is connected to an observation light source control unit 26, and the stroboscopic light source 13 is connected to an imaging light source control unit 27. Each of the observation light source control unit 26, and the imaging light source control unit 27 is connected to the system control portion 19 that also functions as an emission amount calculation unit 28, so as to perform control such as light amount adjustment and turning on and off of the infrared LED 15 as the observation light source, and to perform control such as light amount adjustment and turning on and off of the stroboscopic light source 13 as the imaging light source. Note that, the observation light source control unit 26 and the imaging light source control unit 27 for controlling the infrared LED 15 and the stroboscopic light source 13 function as an illumination light amount control unit for controlling an illumination light amount as a light amount of illumination light of the illumination unit.

Figure 2:
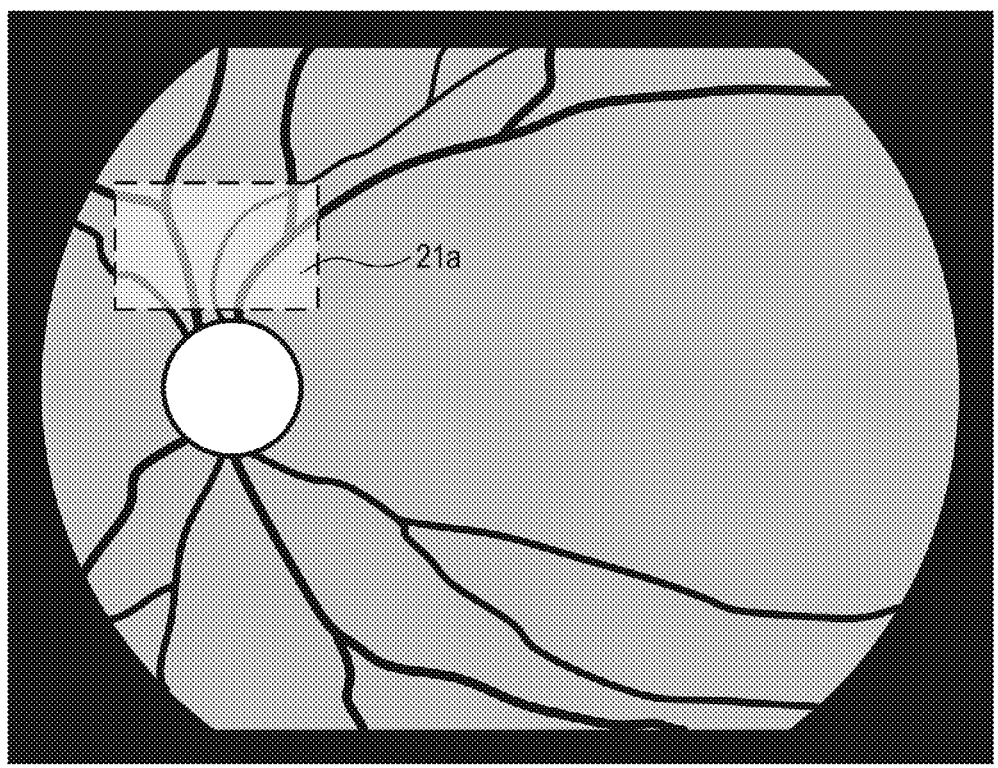
FIG. 2 is a diagram illustrating a fundus image displayed on a monitor 21 and a focus detection area display portion.

FIG. 2 illustrates a fundus observation image displayed on the display monitor 21. In the fundus observation, a focus detection area is displayed to the examiner by a frame portion of a focus detection area display portion 21a so as to be superimposed on the fundus image obtained by the fundus image observation image pickup unit. Thus, it is possible to display a focus detection position to the examiner in a visual manner, and hence operability in the automatic focus can be improved. Note that, the focus detection area can be changed by operation by the examiner, and may be a specific section in the fundus of the eye to be inspected or the entire fundus.

Figure 3:
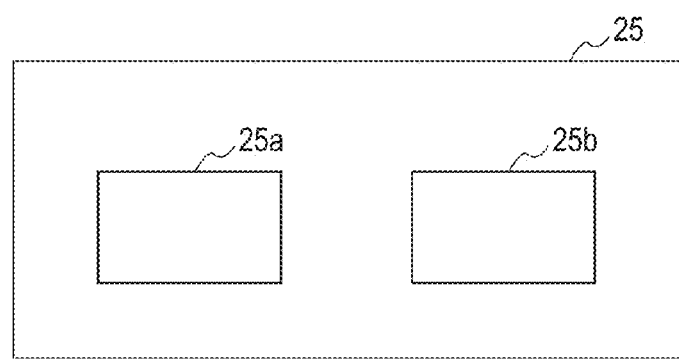
FIG. 3 is a structural diagram of a focus detection portion.

Next, details of the focus detection portion 25 are described with reference to FIG. 3. As illustrated in FIG. 3, the focus detection portion 25 includes a focus detection area determining unit 25a for determining a specific position of the fundus Er as a target of the focus detection. The examiner can determine the focus detection area by operating the operation input portion 24. In other words, the focus detection area is variable. Further, the focus detection portion 25 includes a focus evaluation value storage unit 25b for storing a contrast value of the fundus image and the position of the focus lens 3.

In this embodiment, the focus detection is performed by detecting a contrast value of the fundus image itself formed by imaging rays. Here, the contrast means a luminance difference between neighboring pixels, and the contrast value is a largest luminance difference value in predetermined luminance data.

Figure 4:
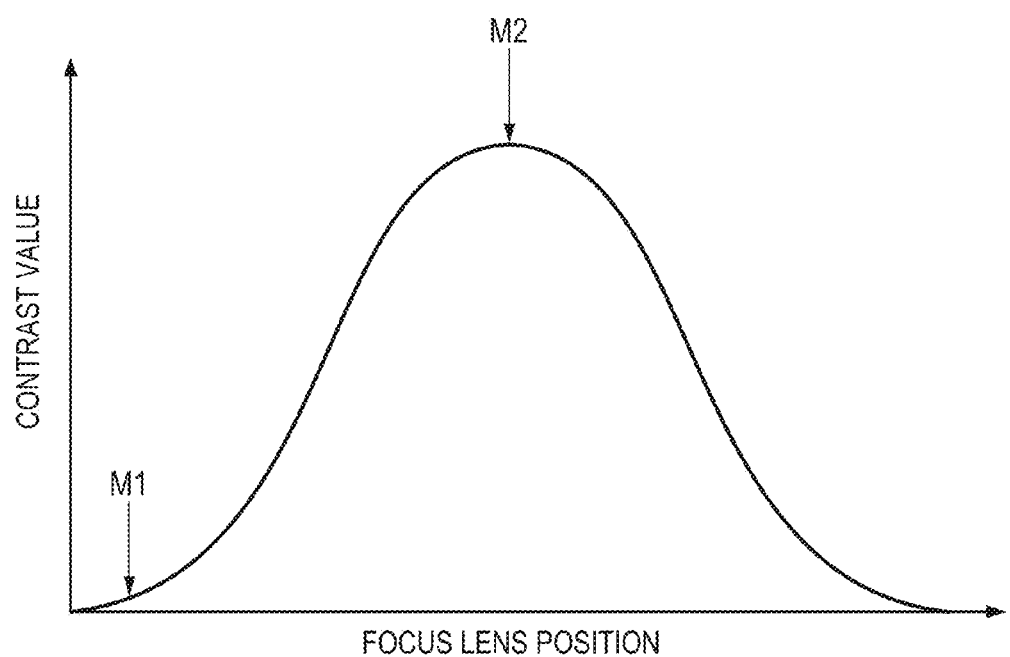
FIG. 4 is a principle diagram of contrast detection.
Figure 5:
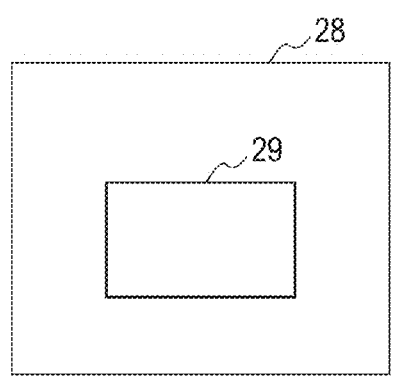
FIG. 5 is a structural diagram of an emission amount calculation unit.

A graph of FIG. 4 shows a transition of the contrast value with respect to the position of the focus lens 3 moved by the focus lens moving portion 6. As is clear from the graph, the contrast value becomes maximum at a focus position M2, while the contrast value is decreased at a position M1 that is significantly out of focus. The focus position M2 is a position at which the fundus image displayed on the monitor 21 can be observed most clearly and is also a position at which the fundus image can be most clearly displayed on the monitor 21 after imaging. Therefore, in this embodiment, it is possible to perform the focus detection without being affected by aberration of the eye to be inspected by using this principle of the contrast detection.

Next, the emission amount calculation unit 28 is described. An output from each pixel of the image pickup element 5 is A/D converted by the A/D converter element 16 and is temporarily stored in the memory 17. The photometry value calculation unit 18 determines a maximum value of luminance values in the focus detection area as a photometry value from pixel outputs stored in the memory 17 and outputs the photometry value to the emission amount calculation unit 28. As illustrated in FIG. 4, the emission amount calculation unit 28 includes a light amount memory 29 (see FIG. 5) storing a reference value of an observation light amount determined to be suited for the focus detection and determines the emission amount of observation light by comparing the photometry value with the reference value. For instance, if the photometry value is higher than the reference value, it is determined that the observation light amount for illuminating the fundus is high. Then, in order to prevent saturation of the luminance value, the emission amount is determined so as to decrease the light amount. On the contrary, if the photometry value is lower than the reference value, it can be determined that the observation light amount for illuminating the fundus is low. Then, in order to facilitate detection of the local maximum value of the contrast value, the emission amount is determined so as to increase the light amount. Note that, the reference value stored in the light amount memory 29 is determined, for example, based on an average reflectance value of the fundus, an average luminance value of specific sections except a vessel portion in the fundus, and the like, so that the luminance value is not saturated.

Next, an operation in this embodiment is described.

Light emitted from the infrared LED 15 is condensed by the condenser lens 14 so as to pass through the dichroic mirror 11, and then the light beam is restricted in a ring shape by the ring stop 10. The light restricted by the ring stop 10 once forms an image of the ring stop 10 on the perforated mirror 7 after passing through the lens 9 and the lens 8. In addition, the light is reflected by the perforated mirror 7 in the direction of the optical axis L1. Further, the light forms an image of the ring stop 10 again in a vicinity of the pupil Ep of the eye to be inspected E by the objective lens 1 and illuminates the fundus Er of the eye to be inspected E.

The light beam, which is reflected and scattered by the fundus Er illuminated by the light from the infrared LED 15 emitting the stationary light, exits the eye to be inspected E through the pupil Ep. Further, the light beam passes through the objective lens 1, the imaging stop 2, the focus lens 3, and the imaging lens 4, and reaches the image pickup element 5 to form an image. An output from the image pickup element is converted into a digital signal by the A/D converter element 16, and then the fundus observation image is displayed on the monitor 21 via the image pickup unit control portion 22.

The examiner observes the fundus image displayed on the monitor 21 and uses an operation rod (not shown) so as to align the eye to be inspected E with the fundus camera optical portion. If the apparatus is set to the manual focus mode by a focus mode switching unit (not shown), the examiner performs, by the operation input portion 24, adjustment of the light amount of the infrared LED 15 so that the fundus has an appropriate brightness and adjustment of the position of the focus lens 3 in the direction of the optical axis L1 while observing the fundus image displayed on the monitor 21. After that, an imaging switch (not shown) in the operation input portion 24 is pressed so as to perform imaging.

When the examiner presses the imaging switch, the stroboscopic light source 13 emits pulse light. The light beam emitted from the stroboscopic light source 13 is condensed by the condenser lens 12 and is reflected by the dichroic mirror 11. Then, the light beam is restricted into a ring shape by the ring stop 10. The light restricted by the ring stop 10 once forms an image of the ring stop 10 on the perforated mirror 7 after passing through the lens 9 and the lens 8. In addition, the light is reflected by the perforated mirror 7 in the direction of the optical axis L1, and forms an image of the ring stop 10 again in a vicinity of the pupil Ep of the eye to be inspected E by the objective lens 1, so as to illuminate the fundus Er of the eye to be inspected E. The light beam reflected and scattered by the fundus Er illuminated by the light beam emitted from the stroboscopic light source 13 exits the eye to be inspected E through the pupil Ep. Further, the light beam passes through the objective lens 1, the imaging stop 2, the focus lens 3, and the imaging lens 4, and reaches the image pickup element 5 to form an image. An output of the image pickup element is converted by the A/D converter element 16 into a digital signal so as to be stored as a still image in the image memory 20.

Next, a control method when the apparatus is set to the automatic focus mode as a feature of this embodiment is described. As illustrated in FIG. 2, in the automatic focus mode, the focus detection area is displayed by the frame portion of the focus detection area display portion 21a so as to be superimposed on the fundus image obtained by the fundus image observation image pickup unit when the fundus of the eye to be inspected is observed. This obtaining of the fundus image corresponds to an observation step in the present invention. The examiner changes a position of the focus detection area display portion 21a by the operation input portion 24 so as to determine the focus detection area. Next, an automatic focus start switch (not shown) is pressed by the examiner so that the automatic focus is started. Note that, the focus detection area is changed by the operation input portion 24 in this embodiment, but it is possible to automatically determine the focus detection area by the system control portion 19 based on a position of a fixation lamp (not shown), for example.

Figure 6:
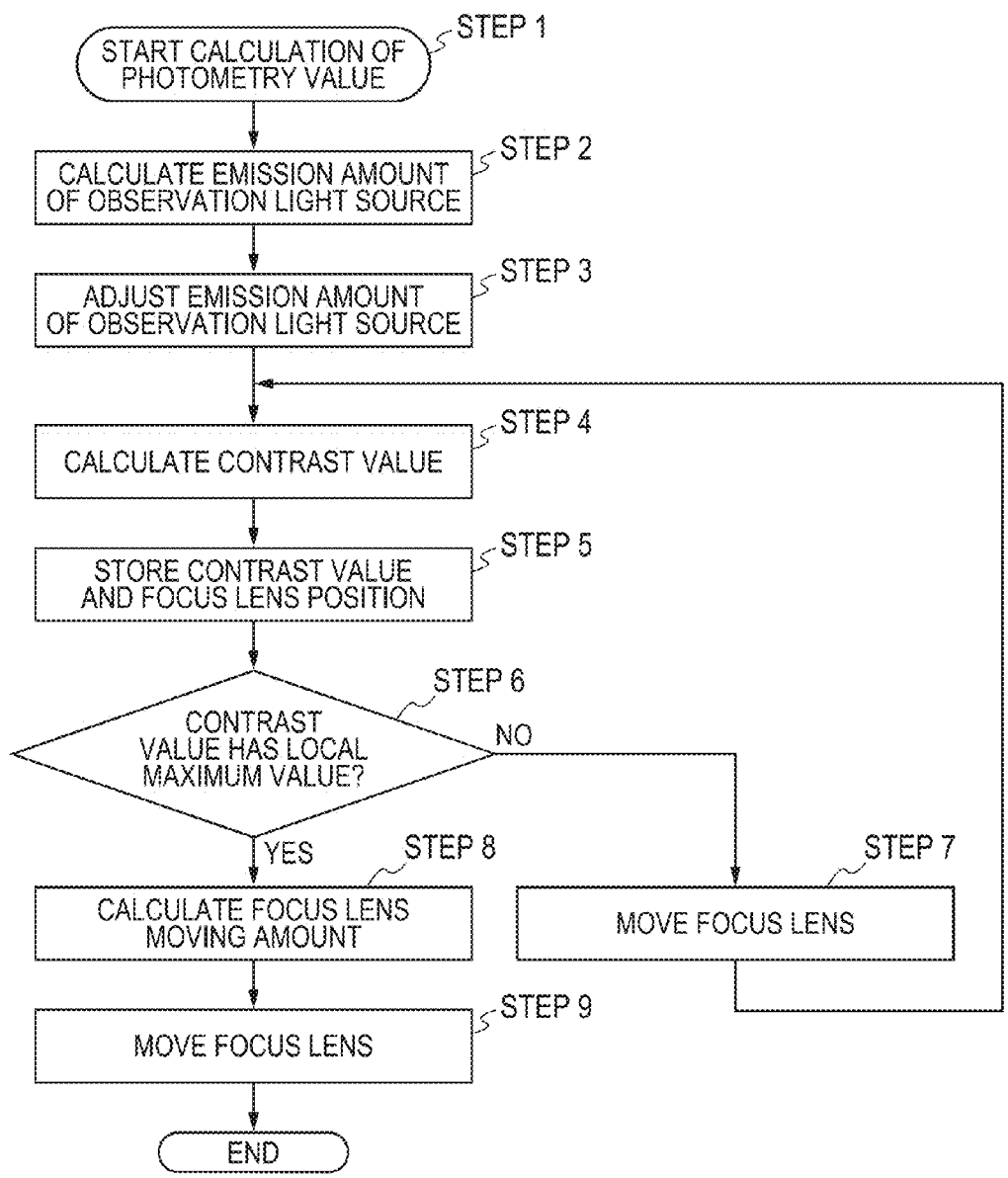
FIG. 6 is a flowchart illustrating the embodiment of the present invention.

The flowchart of FIG. 6 illustrates an operation when the automatic focus is started. When the start of the automatic focus is commanded, in Step 1, as a photometry step, the photometry value calculation unit 18 calculates the maximum value of the luminance value in the focus detection area as the photometry value from the pixel outputs stored in the memory 17 and outputs the photometry value to the emission amount calculation unit 28. In Step 2, as a comparing step, the emission amount calculation unit 28 compares the reference value of the emission amount stored in the light amount memory 29 with the photometry value calculated in Step 1, so as to determine the emission amount of the observation light. Step 3 is performed by the observation light source control unit 26 as the light amount control step, and the fundus is irradiated with the observation light having the light amount determined in Step 2. In Step 4, calculation of the contrast value is performed by the focus detection portion 25. In Step 5, the focus evaluation value storage unit 25b of the focus detection portion 25 stores the contrast value calculated in Step 4 and the position of the focus lens 3. In Step 6, whether or not the local maximum value as the position M2 illustrated in FIG. 3 is included in the contrast value stored in Step 5 is detected.

If the local maximum value is not detected in Step 6, the process proceeds to Step 7. Then, the focus lens 3 is moved by a predetermined moving amount so as to change the focus lens position, and the process of Step 4 and Step 5 is repeated. Next, the process proceeds to Step 6, and it is determined whether or not the local maximum value of the contrast value is detected. After that, Step 7, Step 4, and Step 5 are repeated until the local maximum value of the contrast value is detected in Step 6.

If the local maximum value is detected in Step 6, the process proceeds to Step 8. Step 8 is performed by the focus detection portion 25, and the moving amount of the focus lens 3 is calculated. Here, the moving amount of the focus lens in Step 8 means a driving amount of the focus lens to a position where the local maximum value is detected. Next, in Step 9, the focus lens 3 is moved in accordance with the moving amount of the focus lens calculated in Step 8, and the focus lens 3 is moved to a position of the local maximum value of the contrast value. By the operation performed in the focus step as described above, even if the eye to be inspected E has an individual variation in aberration such as spherical aberration, astigmatism, or the like, it is possible to perform the focus adjustment in accordance with the aberration.

This operation is particularly effective in a non-mydriatic fundus camera for performing observation using infrared light. Because contrast of middle and large blood vessels in the fundus is low with respect to infrared light, a difference of the contrast value with respect to the focus lens position is small. Therefore, it is difficult to detect the position M2 of the local maximum value illustrated in FIG. 4 in the automatic focus. Therefore, it is necessary to increase the light amount of the infrared LED for illuminating the fundus so as to increase the contrast of the observation image as much as possible. However, if the fundus becomes brighter than necessary, the luminance value is saturated so that the contrast value cannot be calculated correctly. However, by calculating and controlling the correct observation light amount before calculating the contrast value using a photometry unit, saturation of the luminance value can be prevented in advance. Thus, the contrast value can be stably calculated so that the focus detection can be performed accurately.

Other Embodiment

Further, the present invention may also be realized by executing the following process. Specifically, software (program) for realizing the function of the embodiment described above is supplied to a system or an apparatus via a network or an arbitrary type of storage medium, and a computer (CPU or MPU) of the system or the apparatus reads and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-229454, filed Oct. 17, 2012, which is hereby incorporated by reference herein in its entirety.

What is claimed is:

1. An ophthalmologic imaging apparatus, comprising:
an illumination unit for illuminating a fundus of an eye to be inspected for observation with an infrared light;
an image pickup unit for imaging the fundus of the eye to be inspected through a focus lens by using reflection light from the fundus illuminated by the infrared light;
an illumination light amount control unit for controlling a light amount of the infrared light;
a focus detection area determining unit for determining a focus detection area with respect to a fundus image taken by the image pickup unit;
a focus detection unit for detecting a focus position of the focus lens in the determined focus detection area;
a photometry unit for calculating a photometry value by using an intensity value of the determined focus detection area; and
a setting unit for setting a focus mode from among (a) a manual focus mode for controlling the focus position of the focus lens in accordance with an operation by an user, and (b) an automatic focus mode for controlling the focus position of the focus lens based on a result of a detection by the focus detection unit,
wherein the illumination light amount control unit controls the light amount to decrease in a case that the photometry value is higher than a reference value, and to increase in a case that the photometry value is lower than the reference value, and
wherein the focus detection unit performs focus evaluation after the light amount is controlled by the illumination light amount control unit.

2. An ophthalmologic imaging apparatus according to claim 1, wherein the photometry unit determines a maximum value of the luminance value in the focus detection area as the photometry value, and
wherein the focus detection unit performs the focus evaluation of the focus detection area after the illumination light amount control unit controls the light amount based on the photometry value.

3. An ophthalmologic imaging apparatus according to claim 1, wherein the focus detection unit detects contrast of a fundus image of the eye to be inspected so as to detect the focus position.

4. An ophthalmologic imaging apparatus according to claim 1, wherein the focus detection area determined by the focus detection area determining unit and an area for calculating the photometry value by the photometry unit are variable, and
wherein the photometry unit determines the area for calculating the photometry value with respect to the focus detection area determined by the focus detection area determining unit.

5. An ophthalmologic imaging apparatus according to claim 1, wherein the illumination light amount control unit further comprises an emission amount calculation unit for determining a light amount of illumination light by comparing (a) the reference value of the reflection light when the illumination unit illuminates the fundus with fl)) the photometry value, and
wherein the reference value is determined based on an average reflectance of the fundus.

6. An ophthalmologic imaging apparatus according to claim 1, further comprising an emission amount calculation unit for determining a light amount of illumination light by comparing (a) the reference value of the illumination light when the illumination unit illuminates the fundus with (b) the photometry value, wherein the illumination light amount control unit controls the light amount of the illumination light in accordance with determination of the emission amount calculation unit, to decrease in a case that the photometry value is higher than the reference value, and to increase in a case that the photometry value is lower than the reference value.

7. An ophthalmologic imaging method, comprising:

an observation step of imaging a fundus image of a fundus of an eye to be inspected through a focus lens by using reflection light from the fundus illuminated by infrared light;

a setting step of setting a focus mode from among (a) a manual focus mode for controlling a focus position of the focus lens in accordance with an operation by an user, and (b) an automatic focus mode for controlling the focus position of the focus lens based on a result of a detection by a focus detection unit;

a focus detection area determining step of determining a focus detection area with respect to the fundus image imaged by the observation step;

a photometry step of calculating a photometry value by using an intensity value of the determined focus detection area;

a light amount control step of controlling a light amount to decrease in a case that the photometry value is higher than a reference value, and to increase in a case that the photometry value is lower than the reference value; and a focus evaluation step of performing focus evaluation after the light amount is controlled.

8. A storage medium for storing a program for controlling a computer to perform the steps of the ophthalmologic imaging method according to claim 7.

9. An ophthalmologic imaging apparatus according to claim 1, wherein, while the focus detection unit performs focus evaluation, the illumination light amount control unit does not control the light amount of the infrared light.

10. An ophthalmologic imaging apparatus according to claim 3, further comprising a drive unit for drive the focus lens to change the focus position, wherein, in a case that the contrast detected is not a local maximum value, the drive unit drives the focus lens and the focus detection unit detects the contrast, without controlling the light amount of the infrared light by the illumination light amount control unit.

11. An ophthalmologic imaging method according to claim 7, wherein, while focusing by the focus lens, the light amount of the illumination light is not controlled.

12. An ophthalmologic imaging method according to claim 7, wherein, before the light amount of the illumination light is controlled, the focusing by the focus lens is not performed.

13. An ophthalmologic imaging apparatus according to claim 3, wherein the focusing is performed by driving the focus lens to the focus position and detecting contrast of the fundus image to detect the focus position, and wherein, in a case that the contrast detected is not a local maximum value, the focus lens is driven and the contrast is detected, without controlling the light amount of the illumination light.

14. An ophthalmologic imaging apparatus according to claim 1, further comprising a display control unit for causing a display unit to display the focus detection area which is capable of being moved on the fundus image by the operation by the user, so as to be superimposed on the fundus image, in a case that the automatic focus mode is set.

15. An ophthalmologic imaging apparatus according to claim 1, wherein in a case that the automatic focus mode is set, the photometry unit calculates the photometry value in accordance with an instruction of starting an automatic focus operation after the focus detection area is determined.

16. An ophthalmologic imaging apparatus according to claim 1, wherein the illumination light amount control unit controls the light amount based on the photometry value so that a luminance value of the fundus is not so high as to result in saturation.

17. An ophthalmologic imaging apparatus according to claim 1, wherein, before the illumination light amount control unit controls the light amount of the infrared light, the focus detection unit does not perform focus evaluation.

* * * * *